United States Patent [19]

Lombard

[11] 4,238,489

[45] Dec. 9, 1980

[54] TREATMENT OF SECONDARY FRIGIDITY

[75] Inventor: Jean-Pierre Lombard, Massy, France

[73] Assignee: C.M. Industries, Paris, France

[21] Appl. No.: 34,971

[22] Filed: May 1, 1979

[51] Int. Cl.$^2$ .................... A61K 31/535; A61K 9/20
[52] U.S. Cl. ................................ 424/248.56; 424/14
[58] Field of Search .................................. 424/248.56

[56] References Cited

PUBLICATIONS

Ornellas, Biochemistry & Pharm., vol. 20, pp. 2141–2147.

Labout et Agressologie, (1969), 10(10), pp. 469–478.
Conn, Current Therapy, 1970 (pp. 671–677).
Ornellas, M. R. et al., Agressologie, 10: 437–449.
Thuret, F. et al., Agressologie, 1970, 11: 417–420.

*Primary Examiner*—Dale R. Ore
*Attorney, Agent, or Firm*—Bacon & Thomas

[57] ABSTRACT

The present invention relates to a process for the treatment of secondary frigidity wherein between 100 and 300 mg of 3-morpholinoethylamino 4-methyl 6-phenyl-pyridazine are administered daily to the patient by oral route.

1 Claim, No Drawings

TREATMENT OF SECONDARY FRIGIDITY

The U.S. Pat. No. 4,169,158, issued Sep. 25, 1979 from application Ser. No. 820,489, filed July 29, 1977, describes a pharmaceutical use of the compound 3-morpholinoethylamino 4-methyl 6-phenyl pyridazine and of the pharmaceutically acceptable salts thereof.

This consists in using the compound as an antidepressant; but it is specified in said patent that this anti-depressive activity has shown some remarkable characteristics in relation to the anti-depressive activity of known anti-depressants.

A first table in the said patent shows the results obtained in clinical tests carried out for a whole series of depressive conditions, such as symptomatic depressive conditions, psychastenia, anxiety neurosis, obsessional neurosis, paranoiac psychosis, schizophrenia, psychomatic diseases occurring in periods of tiredness and strain, and hypochondriac psychosis.

A second table gives the results observed after different clinical tests, and showing that many clinical signs, which are the consequence of the depressive disorders of the treated patients, could be improved when using the anti-depressant described hereinabove.

It has now been found that this same product, namely the 3-morpholinoethylamino 4-methyl 6-phenylpyridazine or 30038, or a pharmaceutically acceptable salt thereof, when administered orally, in doses varying between 100 and 300 mg of active substance per day, could be used for treating secondary frigidity.

By definition, frigidity is (see for example W. L. LINFORD REES—A short textbook of psychiatry—1967):

" . . . a lack of sexual feeling in women and may vary in degree from an intense feeling of revulsion to any sexual advance, to varying sexual arousal without orgasm. Frigidity may be primary or secondary . . . Secondary frigidity is when a woman has experienced orgasm in the past but is unable to do so now. It may be partial or complete".

The syndrome of secondary frigidity may occur:
-for no apparent reason
-as a side-effect of certain drugs, for example psychotropes (this being an iatrogenic frigidity)
-as an effect of certain organic diseases, or mental diseases or local traumatisms.

The 30038 has been tested directly on women, and 8 typical observations are reported hereinafter.

Amongst the cases tested:
-7 were cases of secondary frigidity with no detectable cause,
-1 was a case of frigidity resulting from a treatment by a psychotrope going back to several months.

The extent of the complaint was checked on the day before the start of the treatment with the 30038 as well as on the 30th day and on the last day of the treatment. The gravity of the syndrome was rated as follows:
0 = no syndrome
2 = discreet and intermittent syndrome
2 = slight but permanent syndrome
3 = net syndrome of average gravity
4 = severe syndrome (virtually total lack of sexual arousal)
5 = total syndrome with complete loss of sexual arousal.

In addition, 7 out of these 8 patients were re-examined (by the same examiner) 15 days and one month after the end of the treatment, in order to assess the persistency of any improvement which could have been noted during the actual treatment.

It should be specified that there is no currently known medicine capable of noticeably improving or of curing cases of either iatrogenic secondary frigidity, or of figidity with not apparent causes.

The only medicinal stimulant of sexual feelings in women is amphetamine, which is toxic and generative of toxicomania. In fact, for a woman to experience libido and orgasm again with amphetamine is an immediate unnatural phenomenon, under the effect of the injection of the product. It is short-lasting and a repetition of this treatment leads to the serious effects known for this drug: exhaustion, anorexia and loss of interest in sexual intercourse in general.

The treatment consisted in using for 30 consecutive days, three 50 mg tablets daily of the active product.

The individual cases are reported hereunder.

Observation 1

Identification: C.F.      Sex: F.
Age: 28
Occupation: Medical-assistant

Diagnosis and gravity of the syndrome: Secondary frigidity developing progressively for over 6 months - Trouble of average intensity at the time, with slight vaginismus (initial score: 3.50).

General medical cause: none ⎫
Local cause: none ⎬ No apparent cause
Medicinal origin: none ⎭
Absence of anxiety or patent depression Treatment: (30038). Treatment period: 30 days
Daily dose: one and a half tablets morning and evening, (i.e. 150 mg/day).
No other associated treatment.

| Evolution under treatment | Initial | after 30 days of 30038 | % of improvement |
|---|---|---|---|
| SCORES | 3.50 | 1.00 | 71.5% |

Observation 2

Identification: C.M.      Sex: F
Age: 35
Occupation: Dietetician

Diagnosis and gravity of the syndrome: Secondary frigidity going back to over a year: syndrome of average intensity revealed mainly by a clear reduction in the quality of the orgasm. (Initial score: 3.00)

General medical cause: none ⎫
Local cause: none ⎬ No apparent cause
Medicinal origin: none ⎭
Absence of anxiety or patent depression Treatment: (30038) - Treatment period: 30 days
Daily dose: one and a half tablets morning and evening (i.e. 150 mg/day)

| Evolution under treattment | Initial | after 30 days of 30038 | % of improvement |
|---|---|---|---|
| SCORES | 3.0 | 1.00 | 66.0% |

Observation 3

Identification: A.R.      Sex: F
Age: 25
Occupation: Student

Diagnosis and gravity of the syndrome: partial secondary frigidity of slight intensity, but permanent and going back to about one year. The main factor in this syndrome is a lowering of libido.

| Evolution under treatment | Initial | after 30 days of 30038 | % of improvement |
|---|---|---|---|
| SCORES | 2.0 | 0.00 | 100% |

General medical cause: none ⎫ No
Local cause: none ⎬ apparent
Medicinal origin: none ⎭ cause
Absence of anxiety and of patent depression

Observation 4
Identification: T.P  Sex: F
Age: 19
Occupation: Student

Diagnosis and gravity of the syndrome: Very important secondary frigidity, characterized by a virtually total deficiency of orgasm. The symptoms set in progressively over 6 months (initial score: 4.0)

General medical cause: none ⎫
Local cause: none ⎬ No apparent cause
Medicinal origin: none ⎭
Absence of anxiety or patent depression Treatment (30038) - Treatment period: 30 days
Daily dose: one and a half tablet morning and evening (i.e. 150 mg/day)
No other associated treatment.

| Evolution under treatment | Initial | after 30 days of 30038 | % of improvement |
|---|---|---|---|
| SCORES | 4.00 | 1.00 | 75% |

Observation 5
Identification: G.Z.  Sex: F.
Age: 30
Occupation: Hotel worker Diagnosis and gravity of the syndrome: Strong secondary frigidity characterized more especially in a virtually complete lack of orgasm (Initial score: 4.0) - Symptons going back to nearly a year.

General medical cause: none ⎫
Local cause: none ⎬ no apparent cause
Medicinal origin: none ⎭
Absence of anxiety and patent depression Treatment: (30038) - Treatment period: 30 days - Daily dose: one and a half tablet morning and evening (i.e. 150 mg/day)
No other associated treatment

| Evolution under treatment | Initial | after 30 days of 30038 | % of improvement |
|---|---|---|---|
| SCORES | 4.0 | 0.0. | 100% |

Observation 6
Identification: R.L.  Sex: F.
Age: 26
Occupation: Psychologist Diagnosis and gravity of the syndrome: Patient treated in June and July 1976 with imipramine which resulted in an important secondary frigidity. The frigidity still persisting three months after the interruption of the imipramine treatment (Initial score: 4.0)

General medical cause: none
Local cause: none
Medicinal origin: yes (imipramine)
Absence of anxiety or depression: After the imipramine treatment the patient is perfectly well balanced from a psychic point of view.
The initial psychiatric test has shown no clear symptoms of anxiety or depression Treatment: (30038) - Treatment period: 30 days. Daily dose: one and a half tablet morning and evening (i.e. 150 mg/day)
No other associated treatment.

| Evolution of treatment | Initial | after 30 days of 30038 | % of improvement |
|---|---|---|---|
| SCORES | 4.0 | 0.0 | 100% |

Observation 7
Identification: S.G.  Sex: F.
Age: 39
Occupation: Housewife

Diagnosis and gravity of the syndrome: A secondary frigidity has set in progressively for two years, characterized by a reduction of the frequency and of the intensity of orgasm, which latter has in actual fact become very rare and low.

General medical cause: none ⎫
Local cause: none ⎬ No apparent cause
Medicinal origin: none ⎭
Absence of anxiety or patent depression

| Evolution under treatment | Initial | after 30 days of 30038 | % of improvement |
|---|---|---|---|
| SCORES | 4.0 | 0.0 | 100% |

Observation 8
Identification: H.G.  Sex: F.
Age: 30
Occupation: Secretary

Diagnosis and gravity of the syndrome: Secondary frigidity which has set in progressively for two years. This frigidity is currently total (score: 5.0): Total absence of sensation during sexual intercourse which are no longer sought.

General medical cause: none ⎫
Local cause: none ⎬ no apparent cause
Medicinal origin: none ⎭
Absence of anxiety and of patent depression:

Treatment: (30038) - Treatment period: 30 days - daily dose: one and a half tablet morning and evening (i.e. 150 mg/day)
No other associated treatment.

| Evolution under treatment | Initial | after 30 days of 30038 | % of improvement |
|---|---|---|---|
| SCORES | 5.0 | 2.0 | 60% |

It is further specified:

on the one hand that no treatment has given rise to any secondary symptoms, and on the other hand, that the patients, when checked about one month after the end of the treatment, all declared that they were still feeling the full benefit of the treatment.

The action of 30038 on frigidity is all the more unexpected that most of the psychotrope drugs which are known and used, have an opposite effect, i.e. they tend to encourage frigidity.

What is claimed is:

1. A method for the treatment of secondary frigidity in women, comprising orally administering daily to the secondarily frigid women from 100 mg to 300 mg of 3-morpholinoethylamino-4-methyl-6-phenylpyridazine or a pharmaceutically acceptable salt thereof.

* * * * *